United States Patent [19]

Bousquet et al.

[11] Patent Number: 4,482,606

[45] Date of Patent: Nov. 13, 1984

[54] ISODIAMETRICAL MICROCAPSULES WITH REGULARIZED DIAMETERS AND PROCESS FOR PRODUCING SAME

[75] Inventors: Hubert Bousquet, Caluire; Jean Bernard Egraz, Lyons; Georges Ravet, St. Genis les Ollieres, all of France

[73] Assignee: Printex, Caluire, France
Printex, Caluire, France

[21] Appl. No.: 356,338

[22] Filed: Mar. 9, 1982

[30] Foreign Application Priority Data

Mar. 9, 1981 [FR] France ................. 81 04800

[51] Int. Cl.$^3$ .................. B01J 13/02; B32B 27/30
[52] U.S. Cl. ..................... 428/402.2; 71/DIG. 1;
106/21; 264/4.1; 264/4.3; 346/214; 424/32;
424/33; 427/213.33; 427/213.35; 427/213.36;
346/215; 428/402.21; 428/402.22; 428/402.24;
428/914
[58] Field of Search ................. 264/4.1, 4.3;
428/402.2, 402.22, 402.21

[56] References Cited

U.S. PATENT DOCUMENTS

| | | | |
|---|---|---|---|
| 2,886,446 | 5/1959 | Kramer et al. | 426/5 |
| 3,585,149 | 6/1971 | Vassiliades et al. | 428/402.2 |
| 3,707,514 | 12/1972 | Vassiliades et al. | 521/65 |
| 3,934,069 | 1/1976 | Atzrott et al. | 264/4.1 X |
| 4,268,411 | 5/1981 | Iwata et al. | 428/402.2 |

*Primary Examiner*—Richard D. Lovering
*Attorney, Agent, or Firm*—McDougall, Hersh & Scott

[57] ABSTRACT

A microencapsulation of varied substances such as aromatic agents, colorings, inks, chemical reactives, pharmaceutical and phytosanitary products, fireproof products, glues, finely dispersed in an aqueous phase, in order to obtain microcapsules that are simulaneously isodiametrical and with regularized diameters, which consists in placing face to place an aqueous solution of polymers and/or hydrosoluble copolymers including at least one of the chemical functions belonging to the group constituted by the radicles —COOH, —OH, —CONH$_2$, —COHNR, —CONRR', —NH$_2$, NHR and —NRR', constituting the material of the capsule containing shell, and a solution of substances to be coated in at least one hydrophobic organic solvent, density close to 1, then submitting the liquid medium thus constituted to a mechanical shearing action corresponding to a shearing coefficient included between 8,000 second$^{-1}$ and 70,000 second$^{-1}$, while the medium is maintained at a temperature between 15° C. and 85° C.

The isodiametrical microcapsules with regularized diameters thus obtained have a particularly attractive application in the manufacturing of registration and transfer materials with paper support by both coating process and impression process, such as Offset.

14 Claims, No Drawings

ISODIAMETRICAL MICROCAPSULES WITH REGULARIZED DIAMETERS AND PROCESS FOR PRODUCING SAME

The invention concerns an improved process for encapsulating substances dispersed in a fluid phase leading to the formation of isodiametrical microcapsules.

It also concerns the new product constituted by the isodiametrical microcapsules, which appellation is meant to define the product that is constituted by the shell formed with a polymer and the substances included therein.

It further concerns the registration or transfer materials that are obtained by continuous deposit, or deposit over areas on at least one face of the support, of a bonded deposit of isodiametrical capsules through enduction or impression processes, paper-making technics as well as technics used in the fields of non-woven fabrics, woven fabrics and plastic films.

The invention lastly concerns the encapsulation of very varied substances such as inks, colorings, various chemical reagents, pharmaceutical, phytosanitary, fireproof products, etc.

The micro-encapsulation technic which allows wrapping solid, liquid or volatile substances, generally reactive to their environment into a small-sized shell is an already well-known one.

The large number of documents published in specialized literature in the field reflects how necessary it is for professionals to keep solid, liquid or volatile substances inside protective containers, so as to have them always at hand for the moment chosen to make use of them, that is to say see that they keep the whole of their properties until they are freed by the bursting or the biodegradation of the shells.

A large number of substances have already been encapsulated, among which appear aromatic agents such as perfumes, colorings, chemical reagents among which reactive colorings, glues and adhesives, phytosanitary agents such as certain biocide agents, fertilizers, etc.

But it should also be observed that many publications describe the use of microcapsules in the field of duplication materials by pressure, such materials as have a paper support, such as simple or multiple documents known as "self-acting chemicals" and "contact chemicals".

The preparation of microcapsules, formed from natural or synthetical polymers, have been described in many publications, consequently to professionals' observations about the advantages they bring.

The first preparation process used on the microcapsule walls, one of the oldest and most utilized, performs coacervation from an aqueous solution of natural absorbent colloids, such as gelatins, gum arabic, but also synthetical ones such as copolymers of methylic polyvinyl ether and maleic acid, as well as carboxymethylcelluloses.

As the process can be used only with low colloid concentrations the encapsulation of substances to be coated can be carried out only in an aqueous medium with a low content of such substances—from 18 to 23%—which makes this encapsulation process particularly expensive.

Beside this first inconvenience, another one can appear that is still more awkward. Indeed, professionals know that many absorbent colloids, either natural or derived from natural products such as carboxymethylcellulose can be destroyed by micro-organisms, that make the walls of produced capsules porous, excluding for instance any prolonged preservation of coated substances sensitive to the ambient atmosphere. Encapsulated substances thus risk oxidizing, coming out of their container, making it doubtful that there is any advantage in encapsulating some substances, especially when they are volatile.

Due to such first inconveniences, professionals have tried to find improved processes for the microcapsule walls, using coating materials that are no longer natural but synthetical and which, after polymerization, remain unaltered by aggressions from micro-organisms, or by chemical agents. Besides, such materials are cheaper that above-mentioned absorbent colloids. In other words, these improved processes propose to produce microcapsule walls that no longer let out the whole or part of the coated substances, and resist pressure or shock better than walls previously made from absorbent colloids.

This is why forming processes of microcapsule walls have been proposed by polymerization "in situ"—that is in the medium in which are the substances to be coated.

One first very simple manufacturing process by polymerization "in situ" of synthetic wall microcapsules consists in dispersing the substance to be coated—liquid or made so by solubilizing it in a solvent—in an aqueous solution containing a soluble precondensate of urea-formaldehyde, then induce polymerization by condensation, and lastly precipitate the polymer formed by adding an acid.

As shown by many experiments carried out for making microcapsule walls, the dispersion of the substance to be coated in the aqueous solution of the urea-formaldehyde precondensate must be continuously stirred while polymerization by condensation occurs. Indeed, if not stirred, the dispersion becomes unstable. It is then observed that the finest drops of the substance to be coated group up due to coalescence, making it practically impossible to regularize their diameters the size of which becomes very irregular, from the very small to the largest. The same happens after encapsulation of the droplets which produce encapsulated products that are of extremely variable sizes.

Now, it is to be wished that the encapsulation process should lead, on the one hand, to encapsulated products of regular dimensions, and the other hand, to the reproduction of such dimensions from one production operation to the other. This improved process was described in the French Pat. No. 2,332,798 which aims at manufacturing microcapsules through coating with finely divided particulate materials by means of polymer shells and consists in preparing a dispersion of such particulate materials in an aqueous medium containing a solution of urea-formaldehyde precondensate, then introducing a mixture soluble in water, of melamineformaldehyde precondensate and a polymer preferably including alcohol, amine, amide, acid or acid derivative groups likely to be cross-linked by the precondensate, and lastly inducing cross-linking of the polymer shells formed round the particulate materials by acid catalysis.

In spite of improvements brought by the process to the various drawbacks specified above, there nevertheless subsists difficulties resulting from a certain degree of heterogeneity in the dispersion which is detrimental to the regularity of the diameter of microcapsules produced. The instability of the dispersion could be reduced through the use of surface active agents as was proposed and described, for instance, in the French Pat. No. 2,093,646. The document suggests an encapsulation process concerning substances finely dispersed in a liquid by means of a surfactive-reactive polymer which first includes dispersing said substance in a dispersing agent in the presence of the surfactive-reactive polymer which can form an insoluble compound in said dispersing agent, then rendering the surfactive-reactive polymer insoluble by inducing the formation of a primary suspension of capsules, and lastly adding the solution of a slightly surface-active aminoplast precondensate in the first suspension, entailing the formation of a secondary suspension of capsules with reinforced walls.

This process is naturally derived from the observation of drawbacks detected in previous publications. The first observation results from the necessity of finely dispersing the solid or liquid substances to be coated in the solution of a soluble condensate by appropriately stirring mechanically in presence of the surfactive-reactive polymer, while the shell is being formed so that the dispersed particules remain so, or the agglomerated ones are again separated from one another before they are coated. It is indeed well-known that the solution of a soluble condensate does not favor the fine dispersion of substances to be coated, and leads to turning out more or less roughly formed capsules which, in any case, show great differences in their diameters. The second observation comes from the fact that adequate stirring applied mechanically so as to create and maintain the state of appropriate dispersion within the solution of the soluble condensate when encapsulating, slows down the formation of the polymer shell, regular and thick, that no longer offers sufficient mechanical strength to bear such stirring without damage, that is without bursting.

Thus, previous processes lead to the first conclusion that it is not possible to make microcapsules with small diameters, and more particularly regular-sized diameters, whatever means put to use in processes applied. Indeed, to obtain a fine and fairly regular dispersion of substances to be encapsulated, the formation medium of said capsules must be submitted to strong stirring, which causes at least a fraction of the microcapsules formed to burst. Consequently, the formation medium of said capsules must undergo stirring in the presence of at least one protective agent which, reducing the dispersion effect, leads to turning out rough-shaped, irregular microcapsules.

Another manufacturing process by "in situ" polymerization of synthetic wall microcapsules has been proposed which consists, according to an interfacial method, in placing a phase containing the substance to be encapsulated and a polycondensation reagent in contact with another phase that cannot mix with the former and contains a second reagent likely to react with it and produce a polycondensate. Now, when the two phases are placed in contact with each other, the reaction between the two compounds takes place at the interface of droplets and the dispersion medium, directly the shell, even very thin, is formed round the droplet, the two compounds are separated from each other, preventing the reaction from going on, and turning out microcapsules the walls of which are not strong.

It is due to this inconvenience in connection with interfacial polymerization that an improved encapsulation process has been proposed in the French Pat. No. 2,433,123 which, a two stage process, advocates first dispersing in an aqueous phase an organic one simultaneously containing a liquid hydrophobic substance to be encapsulated and at least one polyfunctional reagent provided with at least one carbonyl or sulphonyl group, then inducing polycondensation of the hydrophobic reagent with at least one polyfunctional amine, initially inhibited by salification, but the amine functions of which are freed by adding an alkaline agent the strength of which is superior to that of said amine, thus inducing the start of polycondensation. But, as the reaction takes place pratically at the very moment when the dispersion of the organic phase occurs within the aqueous phase containing the absorbent reagent, the process leads to the production of very dispersed diameters that range between 1 and 100 microns.

Thus, reading the various publications dealing with encapsulation processes for the encapsulation of various active substances by means of polymers, reveals numerous difficulties that lead to results that are often disappointing even poor, due to the many inconveniences enumerated above such as lack of strength in the microcapsule walls, difficult dispersion of materials to be coated, polymerization "in situ" of polymers constituting the walls too quickly stopped by interface phenomena within dispersions, lastly production of microcapsules very irregular in size.

Now, though the microcapsule is or can be used in numerous fields of application as specialized literature portends, one of the fields in which it is especially put to use is that of duplicating materials acting by pressure. This is for instance the case of the material called "transfer paper" which, formed in a bundle, is composed of an upper sheet, the back of which is coated with microcapsules containing a solution of chromogen agents, then of intermediate sheets the fronts of which are covered with an auxochrome agent, such for instance as acid clay, phenolic resin, etc. that can react with the chromogen solution, which the backs are covered, like the first sheet, with microcapsules containing said chromogen agents. The pressure exerted on the sheet by typing for instance causes the microcapsules to break, and the chromogen agent thus freed reacts with the auxochrome agent that reveals it by the appearance of a color.

But as widely described by specialized literature, microcapsules can also contain inks, colorings, varied chemical reagents, pharmaceutical products, aromatization agents, pesticides, herbicides, etc. . . . that is any body that can be dissolved in suspension in a liquid phase, or being itself in the fluid form, closed up in a microcapsule with a polymer shell. The microcapsule must preserve its content till it frees itself deliberately by breaking, melting, dissolving its wall, or again in particular cases, by diffusion through the wall of said capsule.

The freeing of the microcapsule content which corresponds to deliberate action must not be caused accidentally by premature breaking of its wall. Such, however, is the case described in specialized literature concerning microcapsules meant for graphic duplicating by pressure, of which it is said that the known processes applied fo their manufacture lead to microcapsules the walls of which are not strong enough: for example, they break when the paper surfaces are being coated according to printing technics such as Offset, Heliogravure and Typography.

As the microcapsules produced according to such processes have diameters that are very different from one another, the risks of accidentally breaking the walls by pressure of the microcapsules deposited on a sheet, whether continuous or not, are multiplied by the presence of large-size capsules.

This is why professionals, being unable to find a reasonable solution to the problem raised by the heterogeneity of the diameters of microcapsules produced according to former methods, have tried to protect them when they are being used against accidental breaking and premature freeing of substance contained therein by means of special materials such for instance as starch grains, the diameters of which are larger than the largest microcapsule.

To increase strength against the accidental breaking of the microcapsules deposited on the paper support for reprography, it was proposed to cover said support with a protective material mixed with the microcapsules. The base of the material is cellulose fibers and starch grains, which should leave free scope for deliberately breaking the microcapsules by pressure—for example by typing—but would protect them against accidental mechanical actions which occur in rubbing or storage.

The principle followed for such protection consists in applying the microcapsules and productive materials on selected support, and bond them by means of a gelled starch solution. Such process is described for example in the French Pat. No. 2,170,687.

Thus does examining former methods reveal that the microencapsulation processes known to this day produce irregular microcapsules the walls of which are consequently more or less brittle.

Going further in her research, the applicant studied and developed an encapsulation process for various substances finely dispersed in an aqueous phase which drives at obtaining isodiametrical microcapsules containing the substance to be encapsulated, the diameters of which are regularized.

The process, according to the invention, consists in bringing together:

(a) an aqueous solution of polymers and/or hydrosoluble copolymers with at least one of the chemical functions belonging to the group constituted by the following radicals:

$-COOH, -OH, -CO-NH_2, -CO-NH-R,$ $-CO-N{-R \atop -R''}, -NH_2, -NHR$ and $NRR'$, constituting the material of the capsul containing shell, (b) and a solution of the substance to be coated in at least one hydrophobic organic solvent, density close to 1, belonging to the group of polyarylated solvents, (c) then strongly stirring the liquid medium thus formed by dispersing the solvent bearing the substance to be coated within the solvent bearing the coating material. Such process is characterized by the fact that the liquid medium thus constituted is submitted to shearing action corresponding to a shearing coefficient of at least 8000 second$^{-1}$. According to the invention, the shearing action carried out on the liquid medium formed by bringing together and dispersing the solvent bearing the substance to be coated within the solvent bearing the substance to be coated, is defined by a shearing coefficient generally expressed as follows:

$$C = \frac{\phi \times 3.14 \times N}{60 \times e}$$

a relation in which:
— $\phi$ is the diameter expressed in meters of a rotor, such as a turbine,
— n is the number of revolutions developed by the rotor during the unit of time expressed in minutes. and e is the air-gap expressed in meters, measuring the distance between the rotor and a stator constituted by a fixed crown round the rotor. The applicant noted that the shearing coefficient played an important part in the production of isodiametrical microcapsules.

If the shearing coefficient is too low, that is under 8000$^{-1}$, the microcapsules obtained are not isodiametrical, and their diameters show a very wide dispersion 95% of which may be between 1 micron and 50 microns, Besides, the shells of the capsules thus obtained are irregular in thickness, which creates increased failure in wall strength with the larger ones.

It looks as if, as noted by the applicant, the shearing coefficient goes beyond 70,000 second$^{-1}$, a value for which has been noted a non-negligible rate of destruction in formed microcapsules.

This is why the shearing coefficient is preferably selected between 15000 second$^{-1}$ and 45000 second$^{-1}$.

The aqueous solution of polymers and/or copolymers which generate the capsule shell is generally prepared by dissolution when hot of these materials at a temperature between 10° C. and 60° C.

In the same way, the solution of the substance to be coated in a hydrophobic organic solvent, or in a mixture of hydrophobic solvents is generally obtained by dissolution when hot of said substance at a temperature between 10° C. and 150° C., and preferably between 80° C. and 110° C.

The mixture, constituted by the aqueous solution of polymers and/or copolymers that generate the capsule shell and by the solution in the hydrophobic organic solvent of the substance to be encapsulated, is brought to a temperature at least equal to ambient atmosphere, the temperature usually selected being between 15° C. and 85° C., but preferably between 35° C. and 60° C.

Said mixture is then submitted to the shearing action that corresponds to shearing coefficient selected in the intervals previously enumerated, using any means known of professionals.

But the applicant also observed, thanks to the numerous experiments she carried out to study the process as per invention, that it was possible not only to produce isodiametrical microcapsules, but also deliberately regularize the average diameter, thanks to a judicious, accurate choice in above-mentioned interval in the mixture temperature.

Indeed, she noted that according to the temperature the mixture of the aqueous solution of polymers and/or copolymers generating the capsule shell and the hydrophobic solution of the substance to be encapsulated is brought to, the mechanical shearing action applied according to a coefficient value selected in the interval between 8,000 second$^{-1}$ and 70,000 second$^{-1}$ induces the formation of microcapsules the average diameter of which decreases when the temperature of the mixture increases.

This is how the microcapsule average diameter can be decreased, for instance, in a proportion of 5 to 1 when the temperature of mixed solutions, submitted to mechanical shearing action, develops at a ratio of 1 to 1.5.

The time during which the mixture constituted by the aqueous solution of polymers and/or copolymers generating the capsule shell and by the solution within the hydrophobic organic solvent of the substance to be coated is submitted to shearing action as per invention is normally included between 1 and 60 minutes, but preferably between 20 and 35 minutes. Since the parameters enumerated above are selected within intervals indicated previously, the total volume of the mixture constituted by the aqueous solution of the polymers and/or copolymers generating the capsule shell and by the hydrophobic solution of the substance to be coated, submitted as it is to shearing action as per invention, must go through a number of successive passes in the shearing area. It has been possible to establish that the advisable number of passes of said total volume in the shearing area should be between 10 and 200, but preferably between 12 to 55.

The concentration, expressed in % in weight of polymers and/or copolymers of the aqueous solution generating the capsule shell is generally speaking included between 2 and 15%, but preferably between 3 and 8%.

In the same way, the % concentration in weight within the hydrophobic organic solvent of the solubilized substance to be encapsulated is generally included within 20 and 2% and preferably between 10 and 5%, except for the case when the substance to be encapsulated is the hydrophobic organic solvent itself and represents 100% of substance to be encapsulated.

According to process invented, the aqueous solution which contains the polymers and/or copolymers generating the capsule shell is placed in presence of the hydrophobic organic solution containing the substance to be coated in such quantity that the mass ratio of polymers and/or hydrosoluble copolymers and the substance to be coated is included between 0.05 and 0.3.

Indeed, the applicant verified that if, as previous processes had portended, the ratio is lower than 0.05, it is practically impossible to encapsulate for want of polymers and/or copolymer while if the ratio is higher than 0.3, the medium increases considerably in viscosity, preventing the mechanical shearing action from taking place because of the strong decrease in the transmission of corresponding energy and thus leading to insufficient production of microcapsules. This is why the mass ratio of polymers and/or hydrosoluble copolymers and the substance to be coated is preferably fixed in the interval between 0.07 and 0.15.

After the shearing operation, that is after isodiametrical microencapsulation of substance to be coated has been completed it is important that the pH of the microcapsule suspension in the aqueous medium resulting from the treatment should be brought to optimum point to ensure the reticulation of a precondensate added to said suspension in order to insolubilize and consolidate the walls of microcapsules formed. The pH depends on the nature of polymers and/or copolymers selected to form said walls, but also on the nature of precondensates introduced to bring about reticulation. Thus can experimentation easily determine the conditions of the pH specific to each particular case.

And thus has the applicant been able to establish that the advisable pH interval is generally speaking situated between the limits of 3.5 to 7.5, but preferably between 4.8 and 6.5.

The acid serving to adjust pH is not critical and can be selcted for instance out of the group of organic acids such as formic, acetic or oxalic acids, but also out of strong mineral acids, such as hydrochloric acid.

However, if the polymers and/or copolymers soluble in water selected for the microcapsule walls are naturally acid, the quantity of acid necessary to adjust pH can be lower and eventually non-existent.

The precondensate that is introduced as reticulation agent and thus allows insolubilizing the microcapsules produced is selected among those that are well known of professionals, that is for instance formol, formaldehyde, formaldehyde melamines, urea-formaldehydes, glyoxal, glutaraldehyde.

It can be introduced all at once or in small fractions over a certain period, 30 minutes for example.

Lastly, the suspension of the isodiametrical microcapsules thus insolubilized is cooled, which preferably brings medium temperature down to ambient temperature.

Directly the reticulation of coating materials is completed and medium temperature has been lowered to point required, the pH of the isodiametrical microcapsule suspension can be raised to the point of making it alkaline in order to prevent any further reaction of said materials by introducing an aqueous solution of hydroxide or amines soluble in water.

Practically, the process as per invention for the encapsulation of substances finely dispersed in a liquid phase through formation of isodiametrical microcapsules includes the following stages:

(a) Preparing an aqueous solution of polymers and/or hydrosoluble copolymers including at least one of the following functions: OH, COOH, CO—NH2, CONHR, CO—NRR', NH2, NHR, NRR', meant to form the microcapsule shell by dissolution at a temperature between 10° C. and 100° C., 2 to 15% in weight of said polymers and/or copolymers;

(b) Preparing a solution of substance to be coated in at least one hydrophobic organic solvent by dissolution at a temperature between 10° C. and 150° C., from 20 to 2% in weight of said substance when the latter is not the hydrophobic organic solvent itself;

(c) Mixing without stirring the aqueous solution of polymers and/or hydrosoluble copolymers that generate the isodiametrical microcapsules with the organic solvent alone or containing the substance to be coated in solution, according to such quantities that the mass ratio of polymers and hydrosoluble copolymers is included between 0.05 and 0.3;

(d) Adjusting temperature of above mixture till the temperature selected to produce isodiametrical microcapsules at required diameter is obtained;

(e) Submitting mixture above brought to selected temperature to shearing action corresponding to a coefficient amounting to at least 8,000 second$^{-1}$;

(f) Maintaining mixture above under shearing action from 1 to 60 minutes so that the total volume of said mixture may undergo a number of passes between 10 and 200 in the shearing area;

(g) Directly the mechanical shearing action comes to an end, adjusting pH of the isodiametrical microcapsules suspension in the aqueous medium resulting from said action in the interval between 3.5 and 7.5;

(h) Introducing a reticulation agent, such as a precondensate of melamine-formaldehyde, urea-formaldehyde, glyoxal, in abovementioned suspension in order to insolubilize the microcapsule walls and reinforce their mechanical strength;

(i) Lowering the pH of aqueous suspension of microcapsules preferably down to ambient temperature;

(j) Eventually, raising the pH of the aqueous suspension of microcapsules till it is made alkaline.

The polymers and/or hydrosoluble copolymers generating the isodiametrical microcapsule obtained as per process of invention, having at disposal at least one of the hydroxyl functions (—OH), amine: primary (—NH$_2$), secondary (—NHR) or tertiary (—NRR'), or amide: primary (—CONH$_2$), secondary (—CONHR) or tertiary (—CONRR') in which radicles R and R' are alkyls, aryls or alkylaryls, acid (—COOH) or derived from acid.

Examples of polymers and/or favorite hydrosoluble copolymers may be quoted such as polymers and/or copolymers derived from cellulose such as hydroxypropylcellulose, methylhydroxypropyl-cellulose, carboxymethylcellulose; proteins and their derivatives such as gelatins (agar-agar, gum arabic); polymers and/or copolymers based on melamine and formaldehyde, or urea and formaldehyde; polyacids; polyesters; copolymers of anhydrides such as methyl polyvinyl either and maleic anhydride or polyethylene and maleic anhydride; polyacrylamides or copolymers of acrylamide such as copolymers of acrylamide and acrylic acid.

The choice of polymers and/or hydrosoluble copolymers meant to form the coating substance of the microcapsules should be induced not only by their chemical properties such as absence of reactivity towards substance to be coated, but also by their tendency to oppose the formation of a stable dispersion of fine droplets.

Numerous substances can be encapsulated according to the invention process which allows closing up in a capsule that does not react towards the substance materials which may have various forms: liquid, solid, pasty, etc. such as inks, colorings, glues, perfumes, phytosanitary products and pharmaceutical products with retarded effect, chemical reagents, odoriferous materials which it is required to prevent from giving out strong smells before they are used, fireproof products such as derivatives containing bromine freed from microcapsules by thermofusion, etc.

As has already been acid, the substances to be encapsulated are generally solubilized in a hydrophobic organic solvent or a mixture of hydrophobic organic solvents, density close to 1, so that the solutions bearing the coating substance and the substance to be coated can be intimately and strongly stirred up to ensure fine dispersion of both solutions placed in contact with each other. But the substances to be encapsulated may also be introduced into the solution of polymers and/or hydrosoluble copolymers, providing they are not soluble in the medium and do not react chemically towards it. In such a case, the substances to be encapsulated are divided very finely if they are in the solid form or very finely dispersed under the form of microscopic droplets if they are under fluid form. This may be the case for instance in the isodiametrical microencapsulation of a hydrophobic organic solvent.

Hydrophobic organic solvents used as solubilization agents for the substance to be coated generally belong to the important groups, whether substituted or not, of alkyls, halogenated alkyls, alkyl phosphates, alkyl aryls, aryls, polyaryls alkyl polyaryls, esters, or mixtures of them such as paraffin oils, chlorinated paraffins, trichlorobenzene, nitrobenzene, trichlorethylphosphate, tricresylphosphate, di-n-butylphtalate, di-n-octylphtalate, maleic acid esters, partly hydrogenated terphenyls, dibenzylbenzene mixtures, linear polyalkylbenzene, 10 to 14 carbon atoms mixed with kerosene, polyhalogenated diphenyls such as trichlorodiphenyl, alkylnaphtalenes, such as mono-isopropylnaphtalene, derivatives from diarylmethane, triarylmethane, liquid polyphenols, petroleum ethers, etc.

As mentioned above, the invention also concerns the new product constituted by the isodiametrical capsules as well as registration or transfer materials sensitive to pressure which are obtained by continuous deposit, or deposit over one area on at least one face of appropriate support, of a bed of isodiametrical capsules as per invention by applying enduction or printing processes, using paper-making and printing technics, as well as technics used in the field of non-woven fabrics, woven fabrics and plastic films.

Thus, in order to turn out multiple so-called "in bundle" documents in the field of papers belonging to the class of autonomous self-copying chemicals, or contact chemicals, the applicant did her best to exploit the isodiametrical microcapsules as per invention by developing their application in known processes of superficial treatments given to papers for example from the simplest to the must superficial.

To make up such documents, one technic first used is that of enduction which consists in depositing on at least one face of the paper support a bed of isodiametrical microcapsules in appropriate quantity and regular thickness.

To do so, an aqueous suspension of isodiametrical microcapsules is placed in the feeding area of the enduction sector. Said suspension is formed with isodiametrical microcapsules and fillers such as raw starch, celluloses fibers, and bonds cooked starch, with a concentration amounting to about 40% of dry material.

The suspension of microcapsules is deposited in excess on the paper support by means of various devices such as wetting and taking up by means of a plunger. It is then proportioned and regularly spread on the paper support by means of an appropriate device that eliminates excess.

Various coating process were applied by the applicant which are described hereunder as an illustration.

One first process, called "size-press" and belonging to the class of coating devices fitted with cylinders deposited, proportioned and spread the suspension in one operation in the pressing area. The latter consisted of two horizontal cylinders, one being covered with a hard material, such as rubber, 95° shore hardness, the other with a softer material, 90° shore hardness. The paper support to be coated passed through the two cylinders, one of which at least was a driving one, while the suspension of the isodiametrical microcapsules was directed to the part above the two cylinders, then placed in the tangential space limited by the surfaces of said cylinders. Thus, due to this arrangement, the paper support was coated by the suspension of microcapsules before entering the pressing area of the two cylinders, and the coating suspension was therefore instantly carried at paper speed.

Another process, placed in the category of knife coating devices such for instance as those fitted with an air-knife or with a leveling rotating bar deposited, proportioned and spread the suspension on the paper support in two operations. In the latter case, for instance, the microcapsule suspension was taken up by a coating cylinder, then deposited by contact on the paper support, which cylinder could turn in the same direction as the one along which said support propagated or a different one. The layer deposited was then proportioned and spread by means of a small diameter scraping cylinder turning reversely to the propagation of coated support.

Other coating process, well-known of professionals have also been experimented or are likely to be with excellent results. The following processes come into above-mentioned categories: MASSEY, Reverse Roll, Offset gravure.

Still to turn out multiple documents, so-called "in bundle" having for instance a paper support, by depositing a layer of isodiametrical microcapsules as per invention, the applicant need another technic: the impression one which consists in successively transferring the same image on the support while reserving non-printed areas called "resists" on the support.

The applicant experitested various impression processes: Typography, Flexography, Heliogravure and Offset developing a suspension of bonded microcapsules, dry material concentration about 40%, the qualitative composition of which has already been given.

The Typography impression process used a device the incised printing parts of which were at the same height and on the same level: The suspension of isodiametrical microcapsule to be deposited on the paper support, placed in an appropriate container, was taken up by the first cylinder which transferred it by means of a battery of distribution cylinders to the press cylinder which was fitted with a rigid jacketing that bore the embossed image to be reproduced on the paper support, the latter being maintained in contact with said cylinder by a press cylinder.

Another process called the Flexography process was also tested. The device used included a first cylinder that took up the suspension of isodiametrical microcapsules from an adequate container which by contact transferred said suspension to the impression cylinder thas was fitted with a soft jacket embossed with the image to be reproduced. The paper support to be treated was maintained in contact with the impression cylinder thanks to another cylinder called the press-cylinder.

Then the Heliogravure impression process tested by the applicant made use of a device consisting of a press-cylinder the surface of which is incised according to the image to be reproduced. The suspension of isodiametrical microcapsules placed in an appropriate tank was taken up by the incised cylinder when partially immerged by penetrating into the alveolate parts while the excess of suspension was eliminated by means of a scraping device. Lastly, the paper support to be printed was placed directly in contact with the engraved cylinder thanks to a counter-press one.

Lastly, the applicant also used the Offset process. The printing device used had a cylinder to take up some of the suspension of microcapsules placed in an appropriate container then a battery of distribution cylinders transferred the suspension from the taking-up cylinder to the plate-bearing cylinder. Then said cylinder, called "blanket-carrier", rubber-jacketed, ensured the transfer of the impression of the plate-bearing cylinder to the paper support maintained in contact with the "blanket-carrier" by means of a press-roll called "margin cylinder".

However in the particular case of application of the isodiametrical microcapsules as per Offset process, the aqueous phase of the suspension was replaced by at least one organic solvent, preferably absorbent, or by a mixture of solvents belonging for instance to the glycol family, while the isodiametrical microcapsule walls had previously been reinforced. The suspension of isodiametrical microcapsules used in said process were therefore utilized in an organic solvent or a mixture of solvents, with a concentration of dry material amounting to 40%.

Directly the paper support had been coated continuously or per separate areas, if necessary rectified and lastly dried, it was cut up, bundled up and put through a transfer test by typing, allowing the quality of transfer to be measured: it proved excellent to eighth page, while the bundles thus tested showed no stains through accidental or premature bursting of isodiametrical microcapsules deposited.

The invention will be understood better and its scope more easily appreciated thanks to examples given as indications:

EXAMPLE I

In this example, the applicant produced isodiametrical microcapsules as per invention by means of a laboratory micro-pilot.

A 1,500 Milliliter reactor was used, with a vertical axis, "Prolabo" type, fitted with an anchored stirring device and a "Polytron" turbine, type PTA 10/35, diameter: 15 mm.

(a) Preparation of the aqueous solution containing the polymer generating the microcapsule walls 430 ml of deionized water and 21.8 gr. of a solution of NaOH at 50% was introduced into the reactor, and the mixture brought to the temperature of 50° C.

28.5 gr. of a maleic ethylene-anhydride copolymer, average molar mass of about 30,000, over about 5 minutes was then progressively introduced into the above alkaline solution, and thus obtained mixture was submitted to slow stirring during 30 minutes, which time is required for complete dissolution of above-mentioned copolymer.

At the end of dissolution operation, 16.8 gr. of N-Butylamine were added to above mixture to raise the pH of the medium to the value of 9–10 or so, while maintaining it under slow stirring, that is to say 30–50 R/min. of anchor stirring device.

(b) Preparation of the hydrophobic organic solution of substance to be coated

During the same length of time and in another reactor fitted with stirring and heating devices, was prepared the hydrophobic organic solution containing the substance to be coated.

To do so, 286 g. of hydrogenated Terphenyl were introduced into the second reactor and brought to 100° C. under strong stirring, 100 R/min., then 18.9 gr. of a chromogen agent (color-former) to be encapsulated were added in, constituted by the mixture of four colorings entering the composition in the proportion of hereunder percentages in weight.

| | |
|---|---|
| Crystalized purple lactone (Pergascript blue 1 2R) | 21% |
| Benzoyl-Leuco-Methyl blue | 17% |

-continued

| | |
|---|---|
| (Pergascript blue (S 4G) | |
| Phtalide red | 11% |
| (Pergascript red 16B) | |
| Fluorane green | 51% |
| (Pergascript olive IG) | |

All these colorings were taken from the PERGASCRIPT rang of the CIBA-GEIGY Company.

(c) Production of isodiametrical microcapsules

The two above-mentioned mixtures were then obtained, without any stirring, by introducing the hydrophobic organic solution of substance to be coated into the aqueous solution of above-mentioned copolymer contained in the 1,500 ml Prolabo reactor, then temperature of the mixture was set at 50° C.

The mixture of these two solutions was then submitted to a mechanical shearing action corresponding to a shearing coefficient of 45,000 second$^{-1}$ by using the Polytron turbine above-mentioned while maintaining the medium at a temperature of 50° C.±1° C.

After 10 minutes during which were formed the isodiametrical microcapsules, the mechanical shearing action was stopped and replaced by slow stirring caused by the anchored stirring device turning at 30 to 50 R/min.

An aqueous solution of acetic acid was afterwards added to the suspension of the isodiametrical microcapsules thus obtained, which solution constituted by 26 gr of said acid at 80% and 85 gr of dionized water, lowered the pH of the suspension down to 6–6.2 to allow further reticulation of the microcapsule walls.

The suspension thus acidified was maintained under slower stirring and at the temperature of 50° C.±1° C. for an hour and a half.

After that time, 68 gr of an aqueous solution at 45% of a precondensate of melamine formaldehyde was introduced into the aqueous suspension of isodiametrical microcapsules, the temperature was raised to 75° C. and maintained at said level for two hours.

At the end of that time during which the microcapsule walls had reticulated, the temperature of the suspension of reticulated microcapsules was lowered to ambient temperature (20° C.), then 14 gr of an aqueous solution of ammonia at 30% were introduced to bring the medium to a pH of 7.

Thus was obtained an aqueous suspension of microcapsules that had a 41% concentration of active material.

The microcapsules thus produced were isodiametrical as 80% had diameters measuring between 2 and 5 microns and showed no agglomeration, while 80% of the capsules produced through former processes had diameters distributed between 5 and 50 microns, with numerous agglomerates.

EXAMPLE 2

In this example, the applicant turned out isodiametrical microcapsules as per invention by means of an industrial plant.

The reactor used to this effect had a 1,500 mm diameter, was 2,000 mm high, and showed a useful volume of 2 m3. It was fitted with an anchor stirring device, revolving at 12 R/min. and a turbine developing a shearing coefficient of 16,000 second$^{-1}$.

(a) Preparation of the aqueous solution containing the polymer generating the microcapsule walls In said reactor were introduced 1a succession 0.43 m3 of deionized water and 21.8 kg of a solution of NaOH at 50% which were brought to 50° C.±0.5° C. Then were introduced 28.5 kg of copolymer of ethylene and maleic anhydride, molar mass about 30,000, over a period of 5 minutes. The mixture was then submitted to slow stirring for 30 minutes. At the end of the time, 16,8 kg of N-Butylamine were added under slow stirring of medium to bring pH. to value 9–10.

(b) Preparation of the hydrophobic organic solution of the substance to be coated At the same time, the hydrophobic organic solution containing the substance to be coated was prepared by introducing 286 kg of hydrogenated Terphenyl into another reactor fitted with an anchor stirring device and a heating device and bringing temperature to 100° C. while stirring strongly and adding 18.9 kg of an encapsulating chromogen agent (color former) composed of two colorings entering the composition at following percentages in weight:

| | |
|---|---|
| Crystalized purple lactone | 60% |
| Benzoyl leucomethylene blue | 40% |

These colorings belonged to the PERGASCRIPT range of the CIBA-GEIGY Company.

(c) Production of isodiametrical microcapsules

The two above-mentioned solutions were then mixed, without any stirring, by introducing in the 2 m3 reactor some of the hydrophobic organic solution into the aqueous solution that contained the copolymer above-mentioned. The temperature of the mixture was set at 50° C.±0.5° C.

The mixture of the two solutions, maintained at said temperature were then submitted to mechanical shearing action for 27 minutes by using the turbine that corresponded to a shearing coefficient of 16,000 second$^{-1}$. The total volume of the mixture of the two solutions above-mentioned underwent 24 passes in the shearing area.

After said 27 minutes, an aqueous suspension of microcapsules was obtained which was placed under slow stirring to which was added an aqueous solution of acetic acid (26 kg of acid at 80% and 85 kg of deionized water) to bring the pH of the suspension to 6–6.2, and allow the further reticulation of the microcapsule walls.

The acidified suspension of microcapsules was maintained under slow stirring for 1 hour and 30 minutes, then treated by introducing 68 kg of an aqueous solution at 45% of a precondensate of melamine-formaldehyde and was brought to the temperature of 75° C. under slow stirring, and maintained at said temperature for two hours.

After reticulation of the microcapsule walls was completed, the temperature of the microcapsule suspension was lowered to 25° C. and 14 kg of an aqueous solution at 30% of ammonia was introduced to bring the medium pH to 7.

Thus was obtained an aqueous solution of microcapsules at a 41% concentration in active material.

The microcapsules were isodiametrical, without any agglomeration, 80% of them having diameters between 2 and 5 microns, while 50% had average diameters of 3.5 microns and showed no agglomeration.

The diameters of the isodiametrical microcapsules produced as per invention were determined by the application of the COULTNER principle, using an apparatus of the COULTNER-COUNTER type, Mod TA 11.

EXAMPLE 3

This example illustrates the fundamental influence of the temperature on the average diameter of the isodiametrical microcapsules obtained by the invention process which allows setting temperature at will.

By using the 1,500 ml reactor, prolabo type, and operating at exact times and temperatures and according to compositions, stirring action as well as 45,000 second$^{-1}$ shearing action used in Example 1, the applicant carried out 6 tests for the production of microcapsules by submitting the mixed aqueous solution of maleic ethylene-anhydride copolymer and solution of chromogen agent in hydrogenated terphenyl to above-mentioned shearing action, for temperatures varying from 30° C. to 60° C. at time of said action. For each of these tests, the diameters of microcapsules produced were expressed in microns for 50% of them and results obtained are indicated in the table herehunder.

| Number of test | Temperature in °C. during shearing action | Diameter in micron (50% of capsules) |
| --- | --- | --- |
| 1 | 30 | 13.3 |
| 2 | 35 | 9.4 |
| 3 | 40 | 7.0 |
| 4 | 45 | 4.5 |
| 5 | 50 | 3.5 |
| 6 | 60 | 3.0 |

In each of these tests, the microcapsules produced as per invention were isodiametrical, and the raising of temperature in the medium when the mechanical shearing action was applied caused the average diameter of said microcapsules to fall from 4 to 1 for a rise of temperature going from 1 to 2 when using the same 45,000 second$^{-1}$ shearing coefficient during the same shearing period amounting to 10 minutes.

EXAMPLE 4

This example illustrates the making of transfer materials on paper support, of the chemical reactive type, meant to produce an 8 copy bundle duplicate by the coating process with a leveling rotating bar.

In a container fitted with a slow stirring device, a bonded suspension of isodiametrical microcapsules produced as in example 2 was prepared.

This bonded suspension included:
- 780 kg of the suspension of microcapsules at 41% of active materials,
- 153 kg of an aqueous solution at 17% in weight of cooked starch,
- 33 kg of cellulose fibers, average diameter 15 microns,
- lastly, 33 kg of fine raw starch powder, average diameter 15 microns, Then said bonded suspension of microcapsules was introduced into the feed vat of the coating area of laying device fitted with a leveling rotating bar.

The bonded suspension of isodiametrical microcapsules was taken up by a partly immerged coating cylinder, diameter 250 mm, revolving at 25 R/min., then deposited by contact on the back of the paper support, number of grams per m2:52, the front part of which had been previously coated with an acid clay reactive filler according to paper technics well-known of professionals.

The paper support was 1,100 mm wide and passed through at a speed of 200 m/min.

The proportioning and spreading of the layer of bonded suspension of isodiametrical microcapsules deposited on the back of the paper support were ensured by means of a rotating bar, diameter: 8 mm, revolving at a speed of 10 R/min. in the direction reverse to that along which the paper support propagated.

Then the freshly-coated paper support entered a drying tunnel the temperature gradient of which was shared out between 100° and 150° C.

Lastly, the dried paper support was rectified and conditioned according to technics well-known of professionals.

Directly said operations had come to an end, it was verified that the paper support had received a 4 gr/m2 coating on its back.

After support being cut up and bundles made up with 8 sheets, the transfer test was carried out by typing, revealing excellent transmission of print up to the eighth sheet.

The bundles thus tested showed no stains through accidental or premature bursting of the isodiametrical microcapsules manufactured according to the invention process.

EXAMPLE 5

This example illustrates the manufacturing of transfer materials on paper support of the chemical reactive type, meant to produce duplicates in 8 copy bundles according to the Flexographic impression process.

For this application, the same bonded suspension of isodiametrical microcapsules as those prepared and described in example 4. It was placed in appropriate container of the Flexographic impression area of device used.

Said device was composed of a first cylinder taking up the bonded suspension of the microcapsules, diameter 200 mm, with a helicoidal screen-roll with 120 hachures per linear inch, 0.055 mm in depth of cut, turning at a speed of 470 R/min. The cylinder was fitted with a scraping device eliminating the excess of the bonded suspension of the microcapsules.

This taking-up cylinder transferred said suspension by contact to the plate-bearing cylinder, fitted with a non-rigid jacket on which the image to be reproduced was embossed, same diameter as the one above and revolving at the same speed.

The paper support, 40 gr/m2, the front of which had previously been coated per area with an acid clay reactive filler, had its back kept in contact with the plate-bearing cylinder by means of a press-cylinder revolving at the same speed as the latter.

The paper support was 520 mm wide and passed through at a speed of 180 m/min.

When coming out of the impression sector, the paper support went into an infra-red drying device, 1 micron wave-length, developing a 20 KW/H drying power.

The proportioning and spreading of the bonded suspension of isodiametrical microcapsules were very regular and the back of the paper support was coated with a layer representing 7.5 gr/m2 in the areas concerned after impression and drying.

After paper-support being cut up and bundles of 16 sheets made up, a transfer test was carried out which revealed excellent transmission of print up to sixteenth sheet.

After this test, the bundles showed no stains due to premature or accidental bursting of isodiametrical microcapsules as per invention.

EXAMPLE 6

This example illustrates the manufacturing of transfer materials on paper support of the chemical reactive type meant to make duplicates in 8 copy bundles as per the Offset impression process.

For this application, the same aqueous suspension of microcapsules was used as the one produced in Example 1. However, the aqueous phase of said suspension was replaced by monopropylene-glycol, while the isodiametrical microcapsule walls were reinforced with the same copolymer as the one that had served for encapsulation.

The suspension of isodiametrical microcapsules used in the Offset process therefore had the following composition in weight percentage:

| | |
|---|---|
| isodiametrical microcapsules in dry materials: | 45% |
| solvent: monopropylene glycol: | 55% |

The Offset device included a cylinder for taking up the microcapsule suspension placed in an appropriate container, then a battery of distribution cylinders transferred the suspension of isodiametrical microcapsules from the taking-up cylinder to the plate-bearing cylinder, lastly a cylinder called "blanket-carrier" rubber-jacketed, ensured the transfer of the plate impression on the paper support.

Lastly, the paper support was maintained in contact with the "blanket-carrier" thanks to the press-cylinder, called margin-cylinder.

The plate-bearing, "blanket-carrier" and "margin" cylinders had a 22" diameter and rotated at a speed of 100 R/min.

The paper support, 52 gr/m2, the back of which had previously been coated per area with an acid clay reactive filler was maintained on the back side in contact with the "blanket-carrier".

The paper support was 520 mm wide and passed through at a speed of 180 m/min.

When it had come out of the impression area, the paper support passed through an infra-red drying device, 1 micron in wavelength developing a drying power of 20 KW/H.

The proportioning and spreading of the suspension of isodiametrical microcapsules were very regular and the back of the paper support, after impression and drying, were coated with a 4 gr/m2 layer in the areas concerned.

After the 8 sheet bundles has been cut and constituted, the same transfer test by typing was applied as in examples 4 and 5, which revealed a very good transmission of print, even on eighth sheet.

After said test, the bundles showed no stains by accidental or premature bursting of isodiametrical microcapsules as per invention.

We claim:

1. A microencapsulation process for the treatment of substances finely divided in an aqueous phase to simultaneously obtain isodiametrical microcapsules with regular diameters such that 80% of said diameters measure between 2 and 5 microns comprising contacting an aqueous solution of a polymer or hydrosoluble copolymer containing a functional group selected from the group consisting of —COOH, —OH, —CONH$_2$, —CONHR, —CONRR', —NH$_2$, NHR and NRR' wherein R and R' are each organic groups selected from the group consisting of alkyl, aryl and alkylaryl, as the shell of the capsule with a solution of the substance to be coated dispersed in at least one hydrophobic polyaryl solvent and subjecting the resulting liquid medium to a mechanical shearing action corresponding to a shearing coefficient of at least 8000 second$^{-1}$.

2. A microencapsulation process as defined in claim 1 wherein the liquid medium constituted by the solvent bearing the coating material and the solvent bearing the substance to be coated is submitted to a shearing action corresponding to a shearing coefficient between 8,000 second$^{-1}$ and 70,000 second$^1$.

3. A microencapsulation process as defined in claim 1 wherein the liquid medium constituted by the solvent bearing the coating material and the solvent bearing the substance to be coated is brought, before the shearing action, to a temperature selected between 15° C. and 85° C., and then is maintained at this temperature during shearing action.

4. A microencapsulation process as defined in claim 3 wherein the average diameter of the isodiametrical microcapsules is decreased by bringing the liquid medium before shearing action to a temperature selected among the high values of interval chosen and maintaining it at said temperature during shearing action.

5. A microencapsulation process as defined in claim 1 wherein the liquid medium constituted by the solvent bearing the coating material and the solvent bearing the substance to be coated is submitted to shearing action during a period included in the interval between 1 and 60 minutes.

6. A microencapsulation process as defined in claim 1 wherein the total volume of the liquid medium constituted by the solvent bearing the coating material and the solvent bearing the substance to be coated, is submitted to a number of passes within the shearing area included between 10 and 200.

7. A microencapsulation process as defined in claim 1 wherein the aqueous solution of polymers and/or copolymers is prepared by dissolution when hot of these materials at a temperature between 10° C. and 100° C.

8. A microencapsulation process as defined in claim 1 wherein the solution of substances to be coated in at least one hydrophobic organic solvent is obtained by dissolution when hot of said substance at a temperature between 10° C. and 150° C.

9. A microencapsulation process as defined in claim 1 wherein the % concentration in weight of the solution of substance to be coated in at least one hydrophobic organic solvent is included between 20% and 2% and is 100% when the substance to be coated is the hydrophobic organic solvent itself.

10. A microencapsulation process as defined in claim 1 wherein the % concentration in weight of the solution of substance to be coated in at least one hydrophobic organic solvent is included between 10% and 5% and is 100% when the substance to be coated is the hydrophobic organic solvent itself.

11. A microencapsulation process as defined in claim 1 wherein the aqueous solution containing the polymers and/or copolymers, placed in the presence of the hydrophobic organic solvent containing the substance to be coated, is in such quantity that the mass ratio of polymers and/or hydrosoluble copolymers and the substance to be coated is included between 0.05 and 0.3.

12. A microencapsulation process as defined in claim 1 wherein the polymers and/or hydrosoluble copolymers forming the microcapsule shells are selected in the group constituted by polymers and/or copolymers derived from cellulose, proteins and their derivatives, polymers and/or copolymers based on melamine and formaldehyde, urea and formaldehyde, polyacids, polyesters, copolymers of anhydrides, polyacrylamides and copolymers of acrylamide.

13. A microencapsulation process as defined in claim 1 wherein the hydrophobic organic solvent of substance to be coated belongs, whether substituted or not, to the group of alkyls, halogenated alkyls, alkyl phosphates, alkyl aryls, aryls, polyaryls, and esters.

14. Microcapsules which are isodiametrical and having regularized diameters such that 80% of said diameters measure between 2 and 5 microns produced by the process of claim 1.

* * * * *